(12) United States Patent
Sakashita et al.

(10) Patent No.: US 7,608,138 B2
(45) Date of Patent: Oct. 27, 2009

(54) DEVICE FOR MEASURING FILTER PRESSURE LOSS

(75) Inventors: Satoshi Sakashita, Nagoya (JP); Mitsuo Takahashi, Nagoya (JP)

(73) Assignee: NGK Insulators, Inc., Nagoya (JP)

( * ) Notice: Subject to any disclaimer, the term of this patent is extended or adjusted under 35 U.S.C. 154(b) by 721 days.

(21) Appl. No.: 10/581,744

(22) PCT Filed: Nov. 25, 2004

(86) PCT No.: PCT/JP2004/017478

§ 371 (c)(1),
(2), (4) Date: Jun. 6, 2006

(87) PCT Pub. No.: WO2005/057184

PCT Pub. Date: Jun. 23, 2005

(65) Prior Publication Data

US 2007/0163445 A1   Jul. 19, 2007

(30) Foreign Application Priority Data

Dec. 12, 2003   (JP) .............................. 2003-414291

(51) Int. Cl.
*B01D 46/00* (2006.01)
(52) U.S. Cl. .................... 96/421; 210/411; 210/413; 55/283; 55/294; 55/302; 95/279; 95/281; 95/283
(58) Field of Classification Search ................. 210/411, 210/413; 55/302, 467, 283, 294; 95/279, 95/281, 283, 417; 96/421
See application file for complete search history.

(56) References Cited

U.S. PATENT DOCUMENTS

| 4,651,557 A | 3/1987 | Cholet |
| 4,912,964 A | 4/1990 | Ohtsuki et al. |

FOREIGN PATENT DOCUMENTS

| DE | 3642443 A1 * | 6/1988 |
| EP | 0 187 089 | 12/1985 |
| JP | A 61-149845 | 7/1986 |
| JP | A 63-259436 | 10/1988 |
| JP | A 05-261300 | 10/1993 |

(Continued)

*Primary Examiner*—Walter D Griffin
*Assistant Examiner*—Cameron J Allen
(74) *Attorney, Agent, or Firm*—Oliff & Berridge, PLC

(57) ABSTRACT

Provided is an apparatus 1 for measuring pressure loss in a filter 2, which apparatus includes filter holding means 3; fluid passing means; flow rate measuring means; pressure loss measuring means; and a flow path 6 which connects the four means such that a fluid can pass between the means. The apparatus further includes flow rate regulating means having a mainstream path 7; a tributary path 8 which is branched from the mainstream path 7 and communicates with the outside; and one or more flow path opening/closing members 9 capable of, in conjunction with the level of the fluid flow rate as measured through the flow rate measuring means, opening or closing the mainstream path 7 or the tributary path 8 such that the flow path opening ratio of each of the paths varies continuously or intermittently. The apparatus achieves reliable and convenient measurement of pressure loss with the flow rate of the fluid which passes through the filter 2 being maintained at a constant level by the flow rate regulating means.

5 Claims, 5 Drawing Sheets

FOREIGN PATENT DOCUMENTS

| JP | B2 07-37932 | 4/1995 |
| JP | A 209171 | 8/1995 |
| JP | A 09-085386 | 3/1997 |
| JP | A 10-90160 | 4/1998 |
| JP | B2 2807370 | 7/1998 |
| JP | A 2001-305042 | 10/2001 |
| JP | B2 3294589 | 4/2002 |
| JP | B2 3372097 | 11/2002 |

\* cited by examiner

DEVICE FOR MEASURING FILTER PRESSURE LOSS

TECHNICAL FIELD

The present invention relates to an apparatus for measuring pressure loss in a filter, and more particularly to an apparatus for measuring pressure loss in a filter, which achieves reliable and convenient measurement of filter pressure loss at a constant flow rate.

BACKGROUND ART

Diesel particulate filters (DPFs) are widely employed as filters for trapping and removing a particulate matter contained in a soot-containing fluid such as exhaust gas discharged from a diesel engine. A DPF has an inflow end face through which exhaust gas enters, and an outflow end face through which exhaust gas is discharged, and has a honeycomb structure including a plurality of cells which are formed of porous partition walls having numerous pores (through holes), in which the inflow end faces of predetermined cells and the outflow end faces of the remaining cells are alternately sealed. When particulate matter-containing exhaust gas enters into a cell through its inflow end face, the gas flows through porous partition walls which form the cell and serve as filtration layers, and then the gas is discharged through an outflow end face. In this case, the particulate matter is trapped on the porous partition walls.

Generally, such a DPF is provided in the flow path of exhaust gas discharged from an engine. In such a case, physical properties of the DPF, which have no small effect on performance of the engine, must be measured in advance. Specifically, pressure loss in the DPF at a constant flow rate must be measured in advance as a part of specifications of the DPF.

Conventionally, filter pressure loss has generally been measured through the following procedure: a filter to be subjected to pressure loss measurement is provided in a predetermined fluid flow path; a fluid is caused to pass through the filter at a predetermined flow rate by fluid passing means such as a blower; and the fluid differential pressure generated when the fluid passes through the filter is measured (see, for example, Patent Document 1 and Non-Patent Document 1). In such a pressure loss measuring method (apparatus), the flow rate of a fluid has been regulated by, for example, controlling the rotation speed of a blower (i.e., fluid passing means) by means of an inverter. The apparatus described in Non-Patent Document 1 is basically employed for evaluating the tuning of an air supply/exhaust system of a vehicle engine or the like, and for performing relative comparison of pressure loss on the basis of the flow rate level with respect to a predetermined pressure loss value. Therefore, this apparatus cannot be employed for subjecting numerous DPFs to pressure loss measurement at a constant flow rate, thereby evaluating variations in DPF pressure loss.

Since the filter pressure loss to be measured slightly differs from filter to filter, when pressure loss is to be measured while the flow rate of a fluid is maintained constant, the rotation speed of a blower must be finely regulated for different filters. However, in the case where numerous filters are required to be subjected to pressure loss evaluation in mass production equipment, difficulty is encountered in finely regulating the rotation speed of a blower for different individual filters within a short period of time, and in obtaining reliable measurement results with few errors. In addition, difficulty in finely regulating the blower rotation speed requires an intricate measurement process, which poses a problem in that difficulty is encountered in subjecting numerous filters to pressure loss measurement.

Patent Document 1: Japanese Patent No. 2807370
Non-Patent Document 1: [online], SuperFlow Corporation, [Searched on Dec. 12, 2003], Internet <URL: http://www.superflow.com>

DISCLOSURE OF THE INVENTION

In view of the problems involved in the aforementioned conventional techniques, an object of the present invention is to provide an apparatus for measuring pressure loss in a filter, which achieves reliable and convenient measurement of filter pressure loss at a constant flow rate.

Accordingly, the present invention provides a filter pressure loss measuring apparatus for measuring the differential pressure (pressure loss) of a fluid, which occurs when the fluid passes through a filter having an inflow end face through which the fluid enters and an outflow end face through which the fluid is discharged, the apparatus comprising filter holding means capable of holding the filter; fluid passing means for causing the fluid to pass through the filter; flow rate measuring means for measuring the flow rate of the fluid which passes through the filter; pressure loss measuring means for measuring the pressure loss of the fluid, which occurs when the fluid passes through the filter at a flow rate as measured through the flow rate measuring means; a flow path which connects the aforementioned four means such that the fluid can pass between the means; and flow rate regulating means for regulating the flow rate so as to maintain a constant level, the flow rate regulating means having a tributary path which is branched from the flow path (mainstream path) and communicates with the outside, and one or more flow path opening/closing members capable of, in conjunction with the level of the fluid flow rate as measured through the flow rate measuring means, opening or closing the mainstream path or the tributary path such that the flow path opening ratio of each of the paths varies continuously or intermittently, whereby the pressure loss is measured while the flow rate of the fluid which passes through the filter is maintained at a constant level by the flow rate regulating means.

In the present invention, preferably, each of the flow path opening/closing member(s) has a predetermined rotation shaft, has a fan-shaped cross section as viewed in a plane perpendicular to the rotation shaft, and is provided in the mainstream path so as to be rotated about the rotation shaft provided at the pivot of the fan-shaped member, so that when the member is rotated at a predetermined angle in conjunction with the level of the fluid flow rate as measured by the flow rate measuring means, the member can open or close the mainstream path or the tributary path such that the flow path opening ratio of each of the paths varies continuously or intermittently.

In the present invention, preferably, the fluid passing means is a turbo blower having a discharge pressure of 5 kPa or more.

Preferably, the filter pressure loss measuring apparatus of the present invention further comprises measuring means capable of measuring a physical quantity indicative of environmental conditions under which pressure loss in the filter is measured.

In the present invention, preferably, the filter holding means comprises a first holding means element for holding a portion of the filter located on the side of the inflow end face; and a second holding means element for holding a portion of the filter located on the side of the outflow end face, at least one of the first and second holding means elements including one or more tubular elastic sealing members which have, in at least a portion thereof, a hollow portion and are provided to form a ring, and a frame which is provided outside the elastic sealing member(s), wherein, when an end portion of the filter including the inflow end face and/or the outflow end face is placed inside the elastic sealing member(s), and gas or liquid is brought into the hollow portion of the elastic sealing member(s), the elastic sealing member(s) expand(s), and close contact is established between a peripheral surface of the filter and the elastic sealing member(s), between the frame and the elastic sealing member(s), and between the elastic sealing members, whereby the filter is held in position.

DESCRIPTION OF REFERENCE NUMERALS

1. Pressure loss measuring apparatus, 2. Filter, 3a. First holding means element, 3. Filter holding means, 4. Blower, 5. Ultrasonic flowmeter, 6. Flow path, 7. Mainstream path, 8. Tributary path, 9. Flow path opening/closing member, 10. Flow-rectifying nozzle, 11. Static-pressure chamber, 12. Flow-rectifying honeycomb structure, 13. Discharge outlet, 14. Intake silencer, 15. Discharge silencer, 20. Rotation shaft, 21. Servo valve, 30. Hollow portion, 31. Elastic sealing member, 32. Frame, 33a. Inflow end face, 33b. Outflow end face, 34. End portion, 35. Peripheral surface, 40. Filter box, $P_1$, $P_2$, Pressure gauge, T. Thermometer

BEST MODE FOR CARRYING OUT THE INVENTION

An embodiment of the present invention will next be described. It should be understood that the present invention is not limited to the below-described embodiment, and appropriate design modifications, improvements, etc. may be made on the basis of the common knowledge of those skilled in the art without departing from the scope of the present invention.

Figure 1:
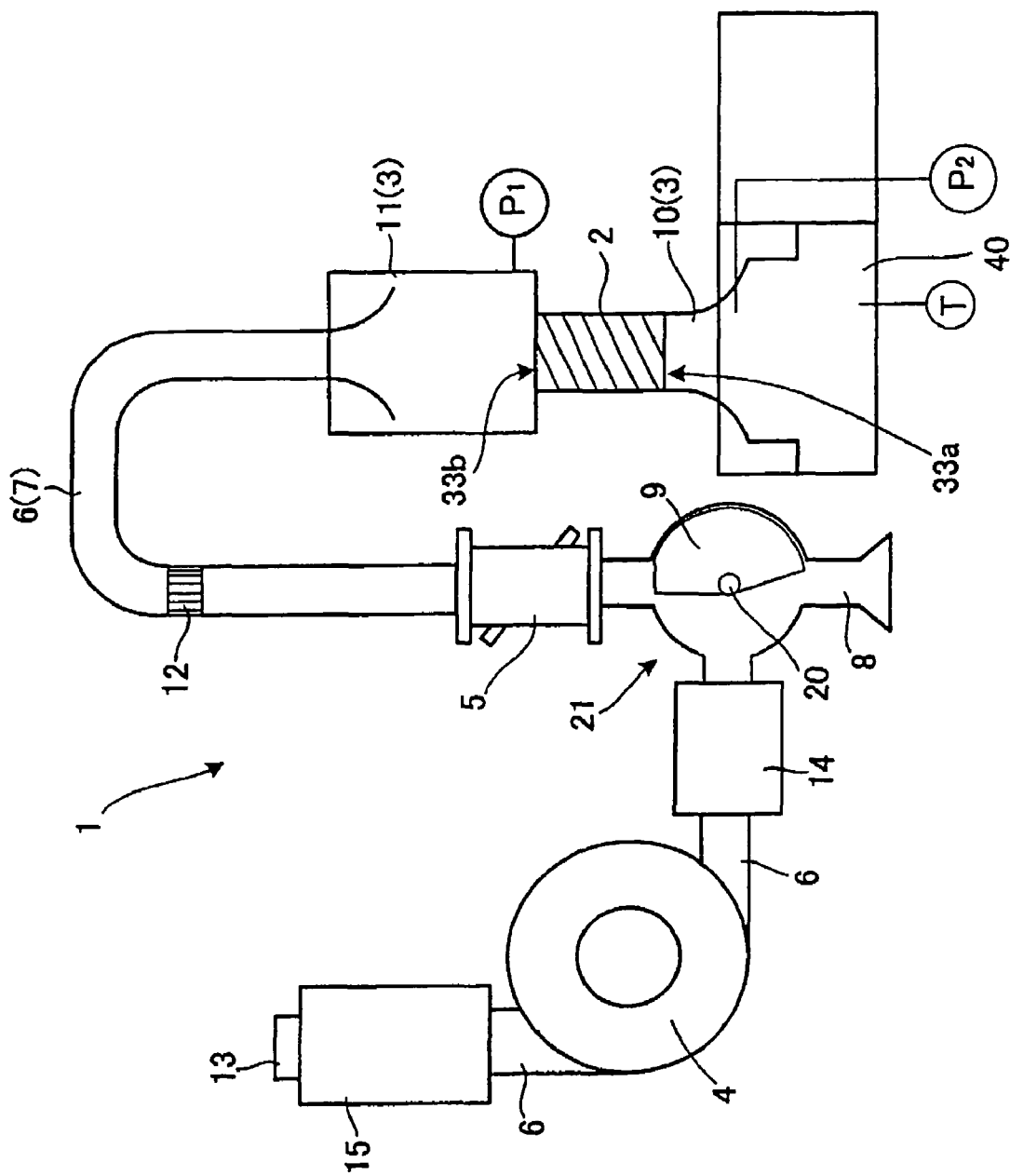
FIG. 1 is a schematic representation showing one embodiment of the filter pressure loss measuring apparatus of the present invention.

FIG. 1 is a schematic representation showing one embodiment of the filter pressure loss measuring apparatus of the present invention. As shown in FIG. 1, the pressure loss measuring apparatus 1 according to the present embodiment includes a flow-rectifying nozzle 10 and a static-pressure chamber 11, which have filter holding means 3 capable of holding a filter 2, or which per se serve as the filter holding means 3. The inflow end face 33a of the filter 2 may be attached to the flow-rectifying nozzle 10, and the outflow end face 33b of the filter 2 may be attached to the static-pressure chamber 11. The filter holding means will be described below in detail.

The flow-rectifying nozzle 10 is connected to a filter box 40 for taking, from the outside, a fluid (e.g., air) which passes through the filter 2 and the entirety of a flow path 6 of the pressure loss measuring apparatus 1. The nozzle 10 has a function of rectifying the flow of air taken from the outside through the filter box 40. The static-pressure chamber 11 has a function of rectifying the flow of air which has passed through the filter 2 and providing the air to the downstream side of the flow path 6, and the chamber 11 is connected to a pressure gauge $P_1$ serving as pressure loss measuring means. Preferably, the pressure loss measuring apparatus 1 according to the present embodiment further includes, on, for example, the filter box 40, measuring means (e.g., a thermometer T or a pressure gauge $P_2$) capable of measuring a physical quantity (e.g., temperature or atmospheric pressure) indicative of environmental conditions under which pressure loss in the filter 2 is measured. This is because, provision of such measuring means can reduce measurement errors due to change in measurement conditions, whereby more reliable measurement results can be obtained.

The pressure loss measuring apparatus 1 shown in FIG. 1 also includes a blower 4 serving as fluid passing means for causing a fluid (air) to pass through the filter 2. No particular limitation is imposed on the blower 4, so long as it has performances (e.g., rotation speed (rate) and displacement) in accordance with, for example, the size of the filter 2 to be subjected to pressure loss measurement or the level of pressure loss. Preferably, the rotation speed of the blower 4 can be controlled by means of an inverter. The blower 4 is preferably a turbo blower having a discharge pressure of 5 kPa or more. This is because, such a turbo blower can suppress occurrence of pulsation of a fluid (air) which is caused to pass through the filter, and achieves accurate flow rate setting, as well as pressure loss measurement with few measurement errors. From the viewpoints of suppressing occurrence of pulsation of a fluid (air) which is caused to pass through the filter in a more effective manner, and attaining more accurate flow rate setting, as well as pressure loss measurement with few measurement errors, the fluid passing means to be employed is more preferably a turbo blower having a discharge pressure of 8 kPa or more, particularly preferably a turbo blower having a discharge pressure of 10 kPa or more.

The pressure loss measuring apparatus 1 shown in FIG. 1 also includes an ultrasonic flowmeter 5 serving as flow rate measuring means for measuring the flow rate of air which passes through the filter 2; and the flow path 6 which connects the aforementioned four means (i.e., filter holding means, fluid passing means, flow rate measuring means, and pressure loss measuring means) such that air can pass between the means, and which communicates from the filter box 40 serving as an air intake unit to a discharge outlet 9. The flow rate measuring means to be employed may be any flowmeter (current meter) other than the ultrasonic flowmeter 5 shown in FIG. 1. Preferably, in the flow path 6, flow-rectifying means (e.g., a flow-rectifying honeycomb structure 12) is provided upstream of the ultrasonic flowmeter 5, so as to perform reliable flow rate measurement with few errors.

The pressure loss measuring apparatus 1 shown in FIG. 1 also includes flow rate regulating means (servo valve 21) having a tributary path 8 and a flow path opening/closing member 9. The tributary path 8 is branched from a mainstream path 7, and is a part of the flow path 6 that communicates with the outside of the pressure loss measuring apparatus 1. The mainstream path 7 is a portion of the flow path 6 other than the tributary path 8. The flow path opening/closing member 9 can, in conjunction with the level of the air flow rate as measured by means of the ultrasonic flowmeter 5, open or close the mainstream path 7 or the tributary path 8 such that the flow path opening ratio of each of the paths varies continuously or intermittently.

In the pressure loss measuring apparatus 1 according to the present embodiment, the air flow rate, which slightly varies with the level of pressure loss to be measured in the filter 2, can be maintained constant without any intricate operation (e.g., fine regulation of the rotation speed of the blower 4). Therefore, pressure loss in the filter 2 at a constant flow rate can be measured in a convenient manner, and reliable measurement results of pressure loss with few errors can be obtained.

In the filter pressure loss measuring apparatus 1 according to the present embodiment, preferably, the flow path opening/closing member 9 is configured as shown in FIG. 1. Specifically, the member 9 has a predetermined rotation shaft 20, has a fan-shaped cross section as viewed in a plane perpendicular to the rotation shaft 20, and is provided in the mainstream path 7 so as to be rotated about the rotation shaft 20 provided at the pivot of the fan-shaped member, so that when the member 9 is rotated at a predetermined angle in conjunction with the level of the air flow rate as measured by means of the ultrasonic flowmeter 5, the member 9 can open or close the mainstream path 7 or the tributary path 8 such that the flow path opening ratio of each of the paths varies continuously or intermittently. This is because, the above-described configuration achieves smooth opening/closing of the mainstream path 7 and the tributary path 8 at a time. Preferably, rotation of the flow path opening/closing member 9 about the rotation shaft 20 is performed by means of a servo motor which is driven in conjunction with the level of the air flow rate as measured by means of the ultrasonic flowmeter 5. This is because, employment of such a servo motor achieves automatic measurement of pressure loss.

Figure 2A:
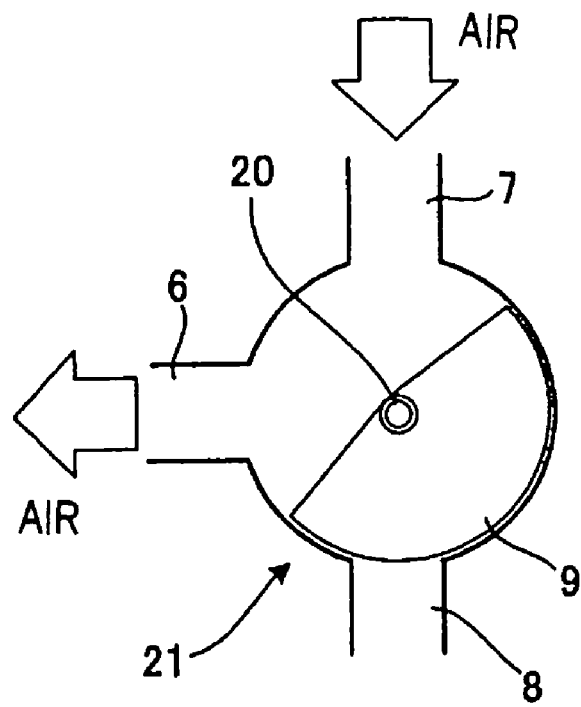
FIG. 2(a) is a schematic representation illustrating the operation of a servo valve constituting one embodiment of the filter pressure loss measuring apparatus of the present invention.
Figure 2B:
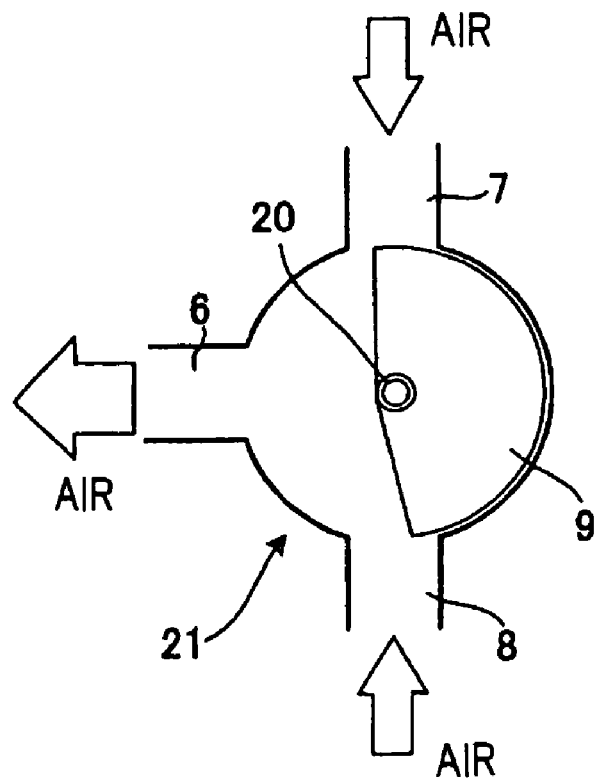
FIG. 2(b) is a schematic representation illustrating the operation of the servo valve constituting one embodiment of the filter pressure loss measuring apparatus of the present invention.

Next will be described operation of the flow rate regulating means (servo valve) constituting the filter pressure loss measuring apparatus according to the present embodiment with reference to FIGS. 2(a) to 2(c). For example, in the case where pressure loss is large in the filter 2 held by the filter holding means, as shown in FIG. 2(a), the flow path opening/closing member 9 is rotated about the rotation shaft 20 at a predetermined angle and then locked such that the mainstream path 7 is opened and the tributary path 8 is closed. Meanwhile, in the case where pressure loss is small in the filter 2, as shown in FIG. 2(a), the flow path opening/closing member 9 is rotated about the rotation shaft 20 at a predetermined angle and then locked such that the mainstream path 7 is partially closed and the tributary path 8 is partially opened. Specifically, since air is taken from the outside into the mainstream path 7 through the tributary path 8, the flow rate of air which passes through the filter can be maintained at a constant level without any intricate operation (e.g., fine regulation of the rotation speed of the blower in accordance with a filter to be subjected to pressure loss measurement). Therefore, pressure loss in the filter at a constant flow rate can be measured in a more convenient manner, and reliable measurement results of pressure loss with few errors can be obtained.

Figure 2C:
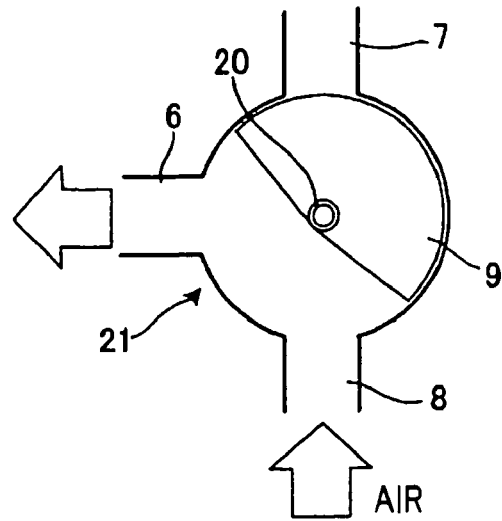
FIG. 2(c) is a schematic representation illustrating the operation of the servo valve constituting one embodiment of the filter pressure loss measuring apparatus of the present invention.

As shown in FIG. 2(c), in the case where the mainstream path 7 is completely closed by means of the flow path opening/closing member 9, since the flow of air which passes through the filter can be stopped, the filter can be exchanged with another filter without stopping the rotation of the blower (i.e., with the blower being rotated continuously). Therefore, numerous filters can be subjected to pressure loss measurement within a short period of time in a convenient manner.

In the pressure loss measuring apparatus 1 according to the present embodiment, preferably, a silencer (an intake silencer 14 or a discharge silencer 15) is provided in the flow path 6 upstream and/or downstream of the blower 4 serving as the fluid passing means, from the viewpoint of noise reduction of the blower 4.

Figure 3A:
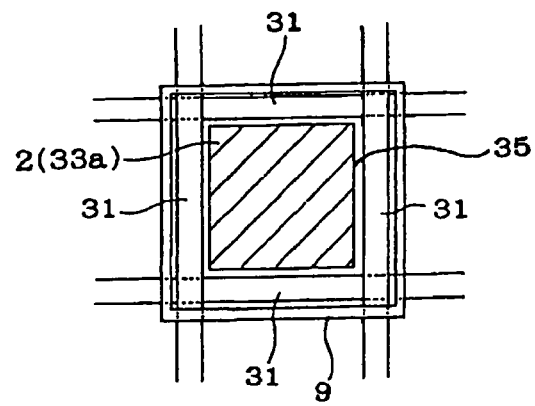
FIG. 3(a) is a bottom view showing an exemplary state of use of filter holding means constituting one embodiment of the filter pressure loss measuring apparatus of the present invention.
Figure 3B:
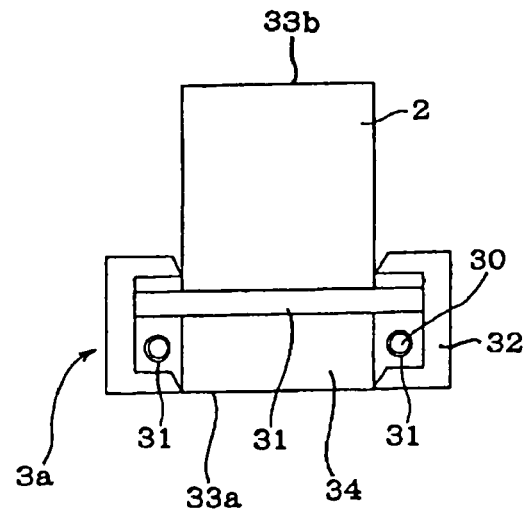
FIG. 3(b) is a side view showing an exemplary state of use of the filter holding means constituting one embodiment of the filter pressure loss measuring apparatus of the present invention, the side view showing the state before the filter is held in position.
Figure 3C:
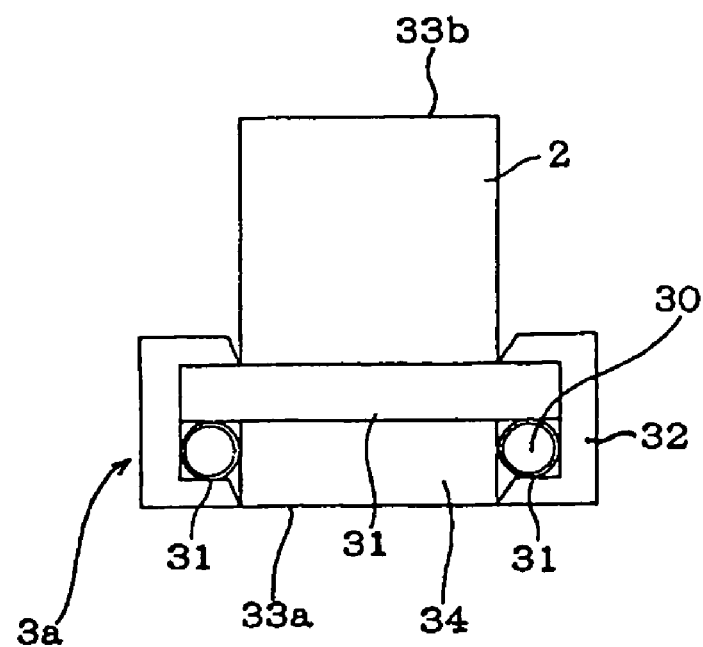
FIG. 3(c) is a side view showing an exemplary state of use of the filter holding means constituting one embodiment of the filter pressure loss measuring apparatus of the present invention, the side view showing the state where the filter is held in position.

Next will be described the filter holding means constituting the filter pressure loss measuring apparatus of the present invention. FIGS. 3(a) to 3(c) show an operational feature of the filter holding means constituting one embodiment of the filter pressure loss measuring apparatus of the present invention. FIG. 3(a) is a bottom view of the filter holding means; FIG. 3(b) is a side view showing the state before the filter is held in position; and FIG. 3(c) is a side view showing the state where the filter is held in position. As shown in FIGS. 3(a) to 3(c), in the present embodiment, the filter holding means includes a first holding means element 3a for holding a portion of the filter 2 located on the side of the inflow end face 33a, and a second holding means element (not illustrated) for holding a portion of the filter 2 located on the side of the outflow end face 33b. FIGS. 3(a) to 3(c) show merely the configuration of the first holding means element 3a, but the second holding means element has a similar configuration.

As shown in FIGS. 3(a) to 3(c), the first holding means element 3a includes four tubular elastic sealing members 31 (each having a hollow portion 30) which are provided to form a ring, and a frame 32 which is provided outside the elastic sealing members 31. For holding the filter 2, firstly, an end portion 34 of the filter (including the inflow end face 33a) is placed inside the elastic sealing members 31 which are provided to form a ring (FIG. 3(a), FIG. 3(b)), and subsequently gas or liquid is brought into the hollow portion 30 of each of the elastic sealing members 31 by non-illustrated pressurization means such as a pump (FIG. 3(c)). When gas or liquid is introduced into the hollow portion 30, the elastic sealing member 31 expands in a radial direction to a predetermined extent. Therefore, close contact is established between the peripheral surface 35 of the filter 2 and the elastic sealing member 31, between the frame 32 and the elastic sealing member 31, and between the elastic sealing members 31 by the mediation of an appropriate abutment pressure, whereby the filter 2 can be held in position.

Conventionally, a filter has been held through a method in which the filter is sandwiched between, for example, holding members with sealing members (e.g., O-rings) being provided on the inflow end face and the outflow end face of the filter, and an appropriate holding pressure is applied in a direction perpendicular to the inflow and outflow end faces. However, this method may encounter difficulty in measuring pressure loss accurately, since the end faces of the filter are partially closed by the O-rings. In contrast, in the case of the filter holding means shown in FIGS. 3(a) to 3(c), which constitutes the pressure loss measuring apparatus according to the present embodiment, the end faces of the filter 2 are not closed, and thus pressure loss can be measured more accurately, which is preferred. With this filter holding means, holding or removal of the filter 2 can be performed through expansion or contraction of the elastic sealing members 31. Therefore, even when filters 2 have a variation in size, pressure loss can be measured without, for example, exchanging the filter holding means per se.

In the present embodiment, preferably, at least one of the first holding means element 3a and the second holding means element has the configuration shown in FIGS. 3(a) to 3(c). More preferably, both the first holding means element 3a and the second holding means element have the configuration shown in FIGS. 3(a) to 3(c). No particular limitation is imposed on the elastic sealing member 31, so long as at least a portion of the member has a tubular form having a hollow portion 30. For example, a portion of the elastic sealing member 31 may be formed of an elastic solid sealing member.

Figure 4:
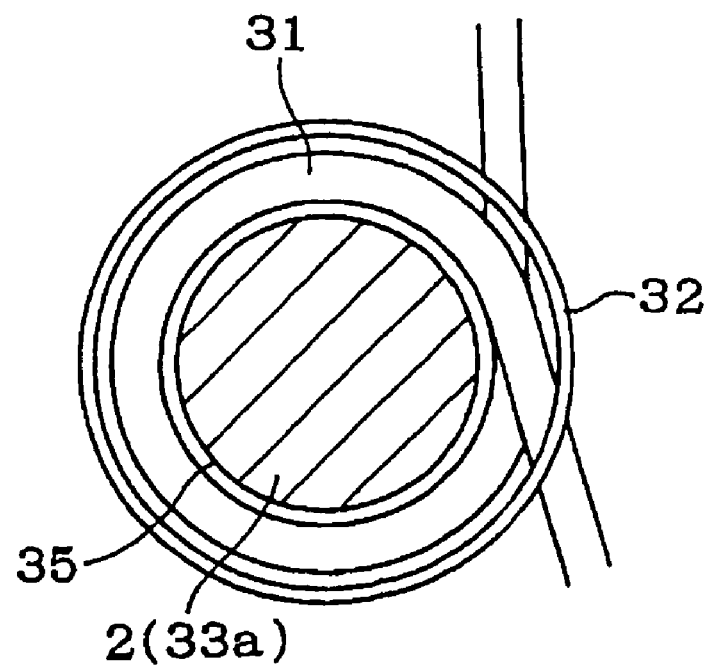
FIG. 4 is a bottom view showing another exemplary state of use of the filter holding means constituting one embodiment of the filter pressure loss measuring apparatus of the present invention.

FIGS. 3(a) to 3(c) show the state where the four elastic sealing members 31 are provided to form a ring. However, a plurality of elastic sealing members 31 may be employed for attaining effective sealing in accordance with the profile of the filter 2 to be held, so long as at least one of the elastic sealing members 31 is provided to form a ring. Specifically, as shown in FIG. 4, when the filter 2 has a circular cross section as viewed in a plane perpendicular to an axis connecting the inflow end face 33a and the outflow end face (not illustrated) of the filter 2, one elastic sealing member 31 may be provided to form a ring.

No particular limitation is imposed on the material constituting the elastic sealing member, so long as when gas or liquid is brought into the hollow portion of the sealing member, the member expands to an appropriate extent and exhibits sealability through close contact between the sealing member and the peripheral surface of the filter, between the sealing member and the frame, and between the sealing members. Specific examples of the sealing member material include low-vulcanized or unvulcanized rubber, closed cell foam rubber, and silicone rubber. No particular limitation is imposed on the material constituting the frame, so long as the material has a strength and hardness enough to withstand the abutment pressure of the expanded elastic sealing member. Specific examples of the frame material include metal, plastic, and ceramic.

Next will be described a method of using the filter pressure loss measuring apparatus of the present invention by taking, as an example, use of the pressure loss measuring apparatus 1 shown in FIG. 1. Firstly, a filter 2 (initial sample) serving as reference is held by the filter holding means 3 as described above. Subsequently, the blower 4 is driven, and air is caused to pass through the filter 2 and the flow path 6. In this case, the air flow rate as measured by means of the ultrasonic flowmeter 5 is monitored while the flow path opening/closing member 9 of the servo valve 21 is rotated, and the rotation speed of the blower 4 is set to a level which achieves effective flow rate regulation through opening/closing of the mainstream path 7 and the tributary path 8.

Thereafter, the filter 2 is sequentially exchanged, and pressure loss is measured. Exchange of the filter 2 can be performed with the mainstream path 7 being closed as shown in FIG. 2(c). Since the flow rate of air which passes through the filter 2 can be regulated by means of the servo valve 21 with the rotation speed of the blower 4 being maintained constant, numerous filters 2 can be conveniently subjected to pressure loss measurement at a constant flow rate within a short period of time. In the case where filters 2 have a large variation in pressure loss, and difficulty is encountered in maintaining the flow rate at a constant level through operation of the flow path opening/closing member 9 of the servo valve 21, the rotation speed of the blower 4 can be re-regulated.

The present invention will next be described in detail by way of an example, which should not be construed as limiting the invention thereto.

EXAMPLE

Example

Figure 5:
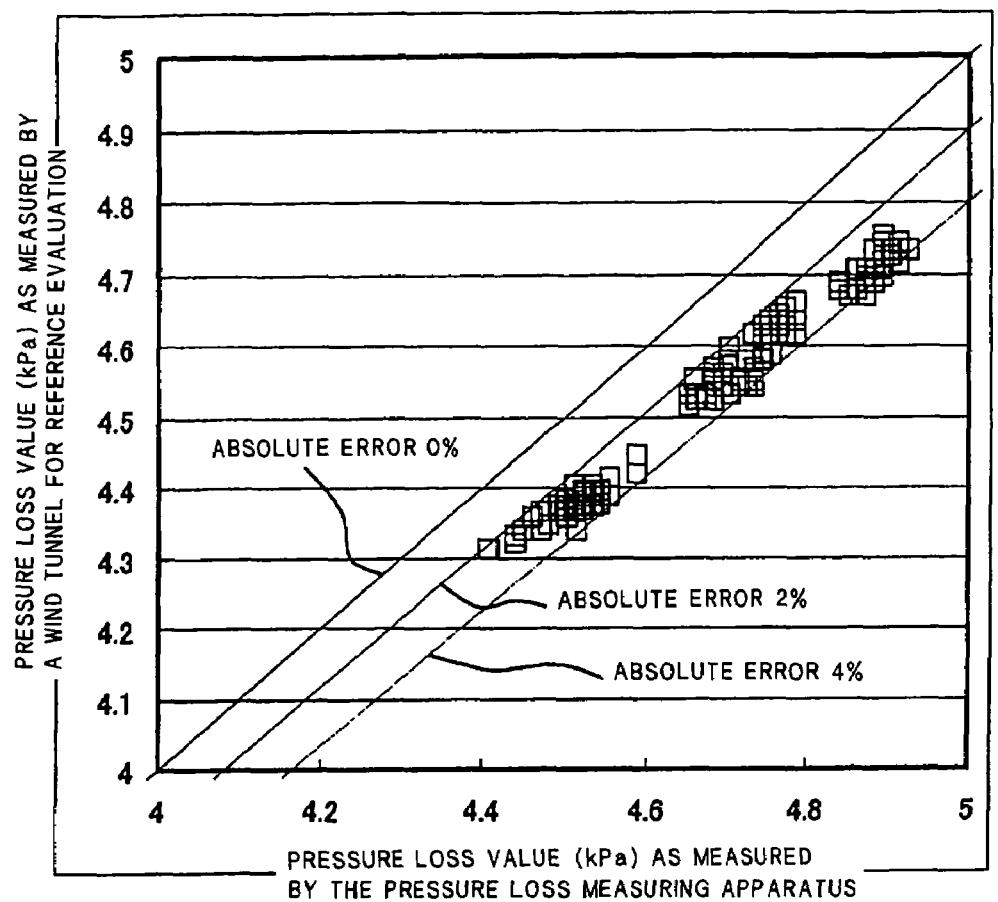
FIG. 5 is a graph in which pressure loss values (kPa) as measured by means of a wind tunnel for reference evaluation are plotted against pressure loss values (kPa) as measured by means of the pressure loss measuring apparatus.

One cylindrical DPF (dimensions: 144 mmφ (outer diameter)×155 mm (total length)) was subjected to pressure loss measurement by means of the pressure loss measuring apparatus 1 shown in FIG. 1. The blower 4 of the pressure loss measuring apparatus 1 was a turbo blower having a discharge pressure of 20 kPa at a flow rate of 20 $Nm^3$/min, and the flow rate was regulated to 9 $Nm^3$/min. The DPF was also subjected to pressure loss measurement through wind tunnel testing by means of a wind tunnel for reference evaluation. FIG. 5 shows a graph in which pressure loss values (kPa) as measured by means of the wind tunnel are plotted against pressure loss values (kPa) as measured by means of the pressure loss measuring apparatus.

Evaluation

The absolute error of the pressure loss values (kPa) as measured by means of the pressure loss measuring apparatus (i.e., measurement values) against the pressure loss values (kPa) as measured by means of the wind tunnel (i.e., reference values) was found to be about 3.15%, and the variation in pressure loss values (i.e., standard deviation σ) was found to be about 0.36%. That is, the pressure loss values as measured by means of the pressure loss measuring apparatus of the present invention were found to have a small error with respect to the pressure loss values as measured by means of the wind tunnel, and to have a very small variation.

Industrial Applicability

The filter pressure loss measuring apparatus of the present invention is employed for measuring the differential pressure (pressure loss) of a fluid, which occurs when the fluid passes through a filter having an inflow end face through which the fluid enters and an outflow end face through which the fluid is discharged. The apparatus includes filter holding means capable of holding a filter; fluid passing means for causing a fluid to pass through the filter; flow rate measuring means for measuring the flow rate of the fluid which passes through the filter; pressure loss measuring means for measuring the pressure loss of the fluid, which occurs when the fluid passes through the filter at a flow rate as measured through the flow rate measuring means; a flow path which connects the aforementioned four means such that the fluid can pass between the means; and flow rate regulating means for regulating the flow rate so as to maintain a constant level, the flow rate regulating means having a tributary path which is branched from a mainstream path and communicates with the outside, and one or more flow path opening/closing members capable of, in conjunction with the level of the fluid flow rate as measured through the flow rate measuring means, opening or closing the mainstream path or the tributary path such that the flow path opening ratio of each of the paths varies continuously or intermittently, whereby the pressure loss can be measured while the flow rate of the fluid which passes through the filter is maintained at a constant level by the flow rate regulating means. Therefore, the apparatus exhibits the effect of achieving enabling reliable and convenient measurement of pressure loss in a filter at a constant flow rate. The apparatus can measure pressure loss in, for example, a DPF (i.e., a vehicle filter) in a convenient manner within a short period of time.

The invention claimed is:

1. A filter pressure loss measuring apparatus for measuring the differential pressure (pressure loss) of a fluid, which occurs when the fluid passes through a filter having an inflow end face through which the fluid enters and an outflow end face through which the fluid is discharged, the apparatus comprising filter holding means capable of holding the filter; fluid passing means for causing the fluid to pass through the filter; flow rate measuring means for measuring the flow rate of the fluid which passes through the filter; pressure loss measuring means for measuring the pressure loss of the fluid, which occurs when the fluid passes through the filter at a flow rate as measured through the flow rate measuring means; a flow path which connects the aforementioned four means such that the fluid can pass between the means; and flow rate regulating means for regulating the flow rate so as to maintain a constant level, the flow rate regulating means having a tributary path which is branched from the flow path (mainstream path) and communicates with the outside, and one or more flow path opening/closing members capable of, in conjunction with the level of the fluid flow rate as measured through the flow rate measuring means, opening or closing the mainstream path or the tributary path such that the flow path opening ratio of each of the paths varies continuously or intermittently, whereby the pressure loss is measured while the flow rate of the fluid which passes through the filter is maintained at a constant level by the flow rate regulating means.

2. A filter pressure loss measuring apparatus according to claim 1, wherein each of the flow path opening/closing member(s) has a predetermined rotation shaft, has a fan-shaped cross section as viewed in a plane perpendicular to the rotation shaft, and is provided in the mainstream path so as to be rotated about the rotation shaft provided at the pivot of the fan-shaped member, so that when the member is rotated at a predetermined angle in conjunction with the level of the fluid flow rate as measured by the flow rate measuring means, the member can open or close the mainstream path or the tributary path such that the flow path opening ratio of each of the paths varies continuously or intermittently.

3. A filter pressure loss measuring apparatus according to claim 1, wherein the fluid passing means is a turbo blower having a discharge pressure of 5 kPa or more.

4. A filter pressure loss measuring apparatus according to claim 1, which further comprises measuring means capable of measuring a physical quantity indicative of environmental conditions under which pressure loss in the filter is measured.

5. A filter pressure loss measuring apparatus according to claim 1, wherein the filter holding means comprises a first holding means element for holding a portion of the filter located on the side of the inflow end face; and a second holding means element for holding a portion of the filter located on the side of the outflow end face, at least one of the first and second holding means elements including one or more tubular elastic sealing members which have, in at least a portion thereof, a hollow portion and are provided to form a ring, and a frame which is provided outside the elastic sealing member(s), wherein, when an end portion of the filter including the inflow end face and/or the outflow end face is placed inside the elastic sealing member(s), and gas or liquid is brought into the hollow portion of the elastic sealing member(s), the elastic sealing member(s) expand(s), and close contact is established between a peripheral surface of the filter and the elastic sealing member(s), between the frame and the elastic sealing member(s), and between the elastic sealing members, whereby the filter is held in position.

* * * * *